(12) United States Patent
Jansen et al.

(10) Patent No.: US 6,638,256 B2
(45) Date of Patent: *Oct. 28, 2003

(54) LOCKABLE SAFETY SHIELD ASSEMBLY FOR A PREFILLABLE SYRINGE

(75) Inventors: Hubert Jansen, Poisat (FR); Claude Imbert, La Tronche (FR)

(73) Assignee: Becton Dickinson France S.A., Le Pont de Claix (FR)

( * ) Notice: Subject to any disclaimer, the term of this patent is extended or adjusted under 35 U.S.C. 154(b) by 186 days.

This patent is subject to a terminal disclaimer.

(21) Appl. No.: 09/767,470

(22) Filed: Jan. 23, 2001

(65) Prior Publication Data

US 2001/0004685 A1 Jun. 21, 2001

Related U.S. Application Data

(60) Division of application No. 09/308,355, filed on May 18, 1999, now Pat. No. 6,193,696, which is a continuation-in-part of application No. 08/941,448, filed on Sep. 30, 1997, now Pat. No. 6,004,296.

(51) Int. Cl.[7] .......................... A61M 5/132; A61M 5/00
(52) U.S. Cl. ..................... 604/198; 604/110; 604/192; 604/196; 604/198; 604/263
(58) Field of Search ............................... 604/181, 187, 604/197, 110, 198, 195, 227, 192, 196, 263

(56) References Cited

U.S. PATENT DOCUMENTS

| 4,425,120 A | 1/1984 | Sampson et al. |
| 4,573,976 A | 3/1986 | Sampson et al. |

(List continued on next page.)

FOREIGN PATENT DOCUMENTS

| AU | A-52050/96 | 2/1996 |
| EP | 0 467 173 A1 | 7/1991 |

(List continued on next page.)

OTHER PUBLICATIONS

Invention Patent, Certificate of Utility, National Institute of Industrial Property, Reg. No. 97 15601.

*Primary Examiner*—Michael J. Hayes
*Assistant Examiner*—Roz Ghafoorian
(74) *Attorney, Agent, or Firm*—David M. Fortunato

(57) ABSTRACT

A lockable safety shield assembly for a prefillable syringe is provided. The design of the lockable safety shield assembly enhances pharmaceutical manufacturers' ease of assembling the various components as part of its filling or processing of the prefillable syringes in normal practice, while at the same time minimizes difficulties in mating parts made from different materials. A tube is placed around the outside surface of the syringe barrel and affixed thereto. A collar is provided on the tube adjacent the distal end of the syringe barrel. A safety shield is axially slidable over the tube between a retracted position, wherein the distal end of the piercing element associated with the prefillable syringe is exposed, and an extended position, wherein the safety shield is locked to the collar to protectively cover the distal end of the piercing element. The safety shield includes locking structure configured so that the shield can be easily fitted over the tube. The locking structure includes at least one deflectable arm provided on the body of the shield. The deflectable arm includes a proximal end deflectable towards the interior of the shield. A stop member is provided on the interior of a shield in spaced relation to the proximal end of the deflectable arm. A ring is axially slidable over the shield to deflect the arm towards the interior of the shield to activate the locking structure. The safety shield is slid distally by an end user such that the collar is lockingly retained between the stop member and the proximal end of the deflectable arm. The collar, the stop member, and the deflectable arm may be configured to provide tactile as well as audible indication of locking to the end user.

36 Claims, 11 Drawing Sheets

U.S. PATENT DOCUMENTS

| | | | |
|---|---|---|---|
| 4,631,057 A | 12/1986 | Mitchell |
| 4,723,943 A | 2/1988 | Spencer |
| 4,737,144 A | 4/1988 | Choksi |
| 4,743,233 A | 5/1988 | Schneider |
| 4,747,837 A | 5/1988 | Hauck |
| 4,758,231 A | 7/1988 | Haber et al. |
| 4,801,295 A | 1/1989 | Spencer |
| 4,826,491 A | 5/1989 | Schramm |
| 4,840,185 A | 6/1989 | Hernandez |
| 4,850,994 A | 7/1989 | Zerbst et al. |
| 4,863,434 A | 9/1989 | Bayless |
| 4,871,355 A | 10/1989 | Kikkawa |
| 4,900,310 A | 2/1990 | Ogle, II |
| 4,917,673 A | 4/1990 | Coplin |
| 4,923,445 A | 5/1990 | Ryan |
| 4,923,447 A | 5/1990 | Morgan |
| 4,927,018 A | 5/1990 | Yang et al. |
| 4,932,937 A | 6/1990 | Gustavsson et al. |
| 4,947,863 A | 8/1990 | Haber et al. |
| 4,985,021 A | 1/1991 | Straw et al. |
| 4,994,045 A | 2/1991 | Ranford |
| 4,998,920 A | 3/1991 | Johnson |
| 4,998,924 A | 3/1991 | Ranford |
| 5,019,051 A | 5/1991 | Hake |
| 5,024,660 A | 6/1991 | McNaughton |
| 5,045,066 A | 9/1991 | Scheuble et al. |
| 5,053,018 A | 10/1991 | Talonn et al. |
| 5,057,086 A | 10/1991 | Dillard, III et al. |
| 5,057,087 A | 10/1991 | Harmon |
| 5,059,185 A | 10/1991 | Ryan |
| 5,066,277 A | 11/1991 | Carrell et al. |
| 5,067,945 A | 11/1991 | Ryan et al. |
| 5,084,030 A | 1/1992 | Byrne et al. |
| 5,106,379 A | 4/1992 | Leap |
| 5,108,378 A | 4/1992 | Firth et al. |
| RE34,045 E | 8/1992 | McFarland |
| 5,137,521 A | 8/1992 | Wilkins |
| 5,141,500 A | 8/1992 | Hake |
| 5,147,303 A | 9/1992 | Martin |
| 5,163,918 A | 11/1992 | Righi et al. |
| 5,169,392 A | 12/1992 | Ranford et al. |
| 5,188,614 A | 2/1993 | Hart |
| 5,197,953 A | 3/1993 | Colonna |
| 5,201,708 A | 4/1993 | Martin |
| 5,201,720 A | 4/1993 | Borgia et al. |
| 5,217,437 A | 6/1993 | Talonn et al. |
| 5,226,894 A | 7/1993 | Haber et al. |
| 5,242,420 A | 9/1993 | Martin |
| 5,256,154 A | 10/1993 | Liebert et al. |
| 5,279,581 A | 1/1994 | Firth et al. |
| 5,300,040 A | 4/1994 | Martin |
| 5,304,149 A | 4/1994 | Morigi |
| 5,308,332 A | 5/1994 | Dillard, III et al. |
| 5,312,365 A | 5/1994 | Firth et al. |
| 5,318,538 A | 6/1994 | Martin |
| 5,318,547 A | 6/1994 | Altschuler |
| 5,338,303 A | 8/1994 | King et al. |
| 5,338,310 A | 8/1994 | Lewandowski |
| 5,342,309 A | 8/1994 | Hausser |
| 5,342,320 A | 8/1994 | Cameron |
| 5,344,407 A | 9/1994 | Ryan |
| 5,346,480 A | 9/1994 | Hess et al. |
| 5,348,544 A | 9/1994 | Sweeney et al. |
| 5,352,208 A | 10/1994 | Robinson |
| 5,356,392 A | 10/1994 | Firth et al. |
| 5,358,491 A | 10/1994 | Johnson et al. |
| 5,380,296 A | 1/1995 | Smedley et al. |
| 5,385,555 A | 1/1995 | Hausser |
| 5,385,557 A | 1/1995 | Thompson |
| 5,417,660 A | 5/1995 | Martin |
| 5,433,712 A * | 7/1995 | Stiles et al. ................. 604/197 |
| 5,437,647 A | 8/1995 | Firth et al. |
| 5,439,450 A | 8/1995 | Haedt |
| 5,447,500 A | 9/1995 | Bergstresser et al. |
| 5,458,577 A | 10/1995 | Kishigami |
| 5,496,286 A | 3/1996 | Stiehl et al. |
| 5,501,672 A | 3/1996 | Firth et al. |
| 5,527,294 A | 6/1996 | Weatherford et al. |
| 5,562,624 A | 10/1996 | Righi et al. |
| 5,562,626 A | 10/1996 | Sampietro |
| 5,601,535 A | 2/1997 | Byrne et al. |
| 5,611,782 A | 3/1997 | Haedt |
| 5,616,134 A | 4/1997 | Firth et al. |
| 5,624,400 A | 4/1997 | Firth et al. |
| 5,647,849 A | 7/1997 | Kalin |
| 5,658,254 A | 8/1997 | Reichenbach et al. |
| 5,674,203 A | 10/1997 | Lewandowski |
| 5,681,292 A | 10/1997 | Tober et al. |
| 5,697,908 A | 12/1997 | Imbert et al. |
| 5,713,871 A | 2/1998 | Stock |
| 5,733,264 A | 3/1998 | Flowers |
| 5,735,823 A | 4/1998 | Berger |
| 5,769,822 A | 6/1998 | McGary et al. |
| 5,769,827 A | 6/1998 | DeMichele et al. |
| 5,776,107 A | 7/1998 | Cherif-Cheikh |
| 5,788,677 A | 8/1998 | Botich et al. |
| 5,792,107 A | 8/1998 | Petrocelli |
| 5,792,122 A | 8/1998 | Brimhall et al. |
| 5,797,885 A | 8/1998 | Rubin |
| 5,800,395 A | 9/1998 | Botich et al. |
| 5,800,403 A | 9/1998 | Pressly, Sr. et al. |
| 5,800,404 A | 9/1998 | Poulsen |
| 5,810,775 A | 9/1998 | Shaw |
| 5,817,064 A | 10/1998 | DeMarco et al. |
| 5,843,034 A | 12/1998 | Redfern et al. |
| 5,843,041 A | 12/1998 | Hake et al. |
| 5,853,390 A | 12/1998 | Freschi |
| 5,855,839 A | 1/1999 | Brunel |
| 5,868,713 A | 2/1999 | Klippenstein |
| 5,873,047 A | 2/1999 | Nakano et al. |
| 5,879,339 A | 3/1999 | Saito |
| 5,882,342 A | 3/1999 | Cooper et al. |
| 5,947,936 A | 9/1999 | Bonds |
| 5,980,494 A | 11/1999 | Malencheck et al. |
| 5,984,898 A | 11/1999 | Garvin |
| 5,984,899 A | 11/1999 | D'Alessio et al. |
| 5,984,906 A | 11/1999 | Bonnichsen et al. |
| 6,004,296 A * | 12/1999 | Jansen et al. ................. 604/198 |
| 6,010,487 A | 1/2000 | DeMichele et al. |
| 6,017,329 A | 1/2000 | Hake |
| 6,030,366 A | 2/2000 | Mitchell |

FOREIGN PATENT DOCUMENTS

| | | |
|---|---|---|
| EP | 0 645 155 A2 | 9/1994 |
| EP | 740 942 A1 | 11/1996 |
| EP | 864 335 A2 | 9/1998 |
| WO | WO 92/19286 | 11/1992 |
| WO | WO 97/14455 | 4/1997 |
| WO | WO 98/35714 | 8/1998 |
| WO | WO 99/16489 | 4/1999 |

* cited by examiner

LOCKABLE SAFETY SHIELD ASSEMBLY FOR A PREFILLABLE SYRINGE

CROSS-REFERENCE TO RELATED APPLICATIONS

This application is a divisional of application Ser. No. 09/308,355 filed on May 18, 1999 now U.S. Pat. No. 6,193,696 which is a continuation-in-part of application Ser. No. 08/941,448 filed on Sep. 30, 1997 now U.S. Pat. No. 6,004,296.

I. FIELD OF THE INVENTION

The invention relates to a lockable safety shield assembly for a prefillable syringe, and more particularly, to a lockable safety shield assembly for a prefillable syringe which is easily attached to a prefillable syringe and which can be subsequently activated by an end-user to form a locking mechanism for the shield.

II. BACKGROUND

As is known in the art, syringes are medical delivery devices utilizable to administer a medicament to a patient. Syringes are normally provided in prefillable form, wherein a set dosage of medicament can be filled into the syringe by a pharmaceutical manufacturer for distribution to the end user, or they are empty and intended to be filled by the end user from a vial or other source of medicament at the time administration of the medicament is desired.

Syringes typically include a barrel portion adapted to retain the medicament. The distal end of the barrel is normally configured to mate with a conventional piercing element, such as a pointed needle cannula made of steel or like material or a blunt ended cannula formed of plastic, to deliver the medicament contained in the barrel. A plunger rod is inserted through the open distal end of the syringe barrel and, through its engagement with an elastomeric or rubber-like stopper element fitted in a fluid-tight manner within the interior of the barrel, a user can apply manual force to the plunger to deliver the medicament through the piercing element.

More typically the case with pointed needle cannulae, accidental needle sticks that occur after the needle cannula has been used generally pose a greater health risk. To avoid such accidents, many prior art hypodermic syringes include a rigid cylindrical safety shield telescoped over the syringe barrel. The prior art safety shield can be slid from a proximal position where the needle cannula is exposed for use, to a distal position where the safety shield protectively surrounds the needle cannula.

Most prior art hypodermic syringes with cylindrical safety shields telescoped over the syringe barrel include structure for locking the safety shield in its distal position. Examples of such structures are found, for instance, in U.S. Pat. Nos. 5,342,309 and 5,385,555 to Hausser and U.S. Pat. No. 5,304,149 to Morigi.

While generally suitable for the tasks employed, further improvements are still being sought. For instance, where the syringe is prefillable by a pharmaceutical manufacturer, it would be beneficial to incorporate improvements into the locking structure employed with the safety shields to better facilitate a pharmaceutical manufacturer's processing of the various components associated with the syringe barrel and safety shield. These improvements should also facilitate the end user's normal use of the prefillable syringe and easy activation of the safety shield once safe disposal of the syringe is desired. Moreover, most of the prior art approaches focus their efforts on employing a plastic collar element on some distal portion of the syringe barrel, with the shield locking onto the collar. While a valid approach, because many of the prefilled syringes currently in use are made of glass, it can be difficult to assemble the plastic collar element onto the syringe barrel. Accordingly, it would be useful to design a structure whereby the collar were incorporated as part of the shield structure itself.

III. SUMMARY OF THE INVENTION

A lockable safety shield assembly for prefillable syringes is provided. The lockable safety shield is designed to facilitate a pharmaceutical manufacturer's assembly of the various components associated with the lockable safety shield onto the syringe in conjunction with how the syringes are normally processed by the pharmaceutical manufacturer. The locking structure associated with the safety shield of the present invention may be designed such that it will not interfere with easy assembly by the pharmaceutical manufacturer, but which can be easily activated by an end user to facilitate safe covering of the distal end of a piercing element once the prefillable syringe has been used.

The assembly includes a tube mounted about the outside surface of the syringe barrel. The tube can be locked, for instance, to the flange provided about the proximal end of the syringe barrel. The tube features a collar positioned adjacent the distal end of the syringe barrel. The collar can be configured as a flat, disk-like structure formed in an annular manner about the outside of the tube.

A safety shield is coaxially mounted over the tube. The safety shield is axially movable between a retracted position, wherein the distal tip of a piercing element affixable to the barrel is exposed, and an extended position, wherein the distal tip of the piercing element will be covered. The safety shield includes a proximal end, a distal end, and a circumferential sidewall therebetween. The circumferential sidewall has an outside surface and an inside surface. Particularly, the shield is provided with user-activatable locking structure to secure the shield in its extended position respective of the syringe.

In one configuration, the locking structure includes at least one deflectable arm incorporated as part of the structure of the sidewall. The deflectable arm includes a distal end mounted with the circumferential sidewall, and a proximal end which is deflectable towards the interior of the shield. At least one stop member is mounted to the interior surface of the shield and spaced a distance from the proximal end of the deflectable arm to define a gap between the stop member and the proximal end of the deflectable arm. The deflectable arm has a free position, wherein the outside surface of the arm is substantially co-planar with the outside surface of the circumferential sidewall, and a locking position, wherein the deflectable arm is urged towards the interior of the shield so that the proximal end of the deflectable arm is positioned towards the interior of the shield.

Means are provided on the shield to activate the locking structure. In one configuration, a circumferential ring is axially slidable about the outside surface of the shield between a first position, wherein the ring is spaced away from the deflectable arm, and a second position, wherein the ring is positioned against the at least one deflectable arm to secure the arm in the locking position. The ring may be secured to the distal end of the shield by a user-severable connection. The user-severable connection may entail, for instance, one or more frangible sections of material provided between the ring and the distal end of the shield. A pair of spaced abutments may be provided on the outside surface of the deflectable arm to retain the ring in its second position.

In practice, the safety shield assembly is typically preassembled by the syringe manufacturer and supplied to the pharmaceutical manufacturer in a sterile state, ready for attachment to the prefillable syringe once it has been filled with a desired drug.

After the syringe has been filled with the drug and otherwise subjected to various processing operations, such as various particulate inspection operations, labeling operations, plunger rod assembly operations, or the like, the safety shield assembly can be easily fitted to the syringe. The tube is fitted about the syringe barrel and clipped onto the flange of the syringe barrel. In the preassembled state, the shield located respective of the tube such that the shield will be placed in a retracted position vis-a-vis the piercing element. Various structures associated with the tube may be provided with sloped surfaces to ensure smooth placement of the safety shield assembly over the syringe flange.

Subsequent to placing the shield assembly onto the syringe barrel, the locking structure must be activated. The locking structure is activated by detaching the ring from its user-severable connection, and sliding the ring proximally so that it is engaged between the abutments provided on the deflectable arm. If desired, the device may be shipped by a pharmaceutical manufacturer to an end user with the ring connected to the shield by its user-severable connection, so that the end-user himself activates the locking structure. Alternately and preferably, the pharmaceutical manufacturer activates the locking structure as part of the assembly process, such that the filled syringe with safety shield assembly is shipped to an end-user with the locking structure already activated.

After the syringe has been used to administer an injection, the shield is slid distally over the tube. The collar will be captured between the proximal end of the deflectable arm and the stop member in order to lock the shield in its extended position. In a preferred embodiment, the deflectable arm, the collar, and the stop member may be configured to provide audible as well as tactile indication to the end user that the shield has been securely locked with the collar.

In a preferred embodiment, at least two deflectable arms are provided. The two deflectable arms are located on diametrically opposite sides of the shield. Correspondingly, two stop members are provided to interact with the two deflectable arms. When viewed along the central axis of the shield, the stop members can be circumferentially aligned with a respective proximal end of the deflectable arms, or they can be circumferentially offset from a respective proximal end.

IV. BRIEF DESCRIPTION OF THE DRAWINGS

The invention will now be described in greater detail by way of reference to the appended drawings, wherein.

V. DETAILED DESCRIPTION OF THE INVENTION

A convention utilized throughout this description is that the term "distal" refers to the direction furthest from a practitioner, while the term "proximal" refers to the direction closest to a practitioner.

Figure 1:
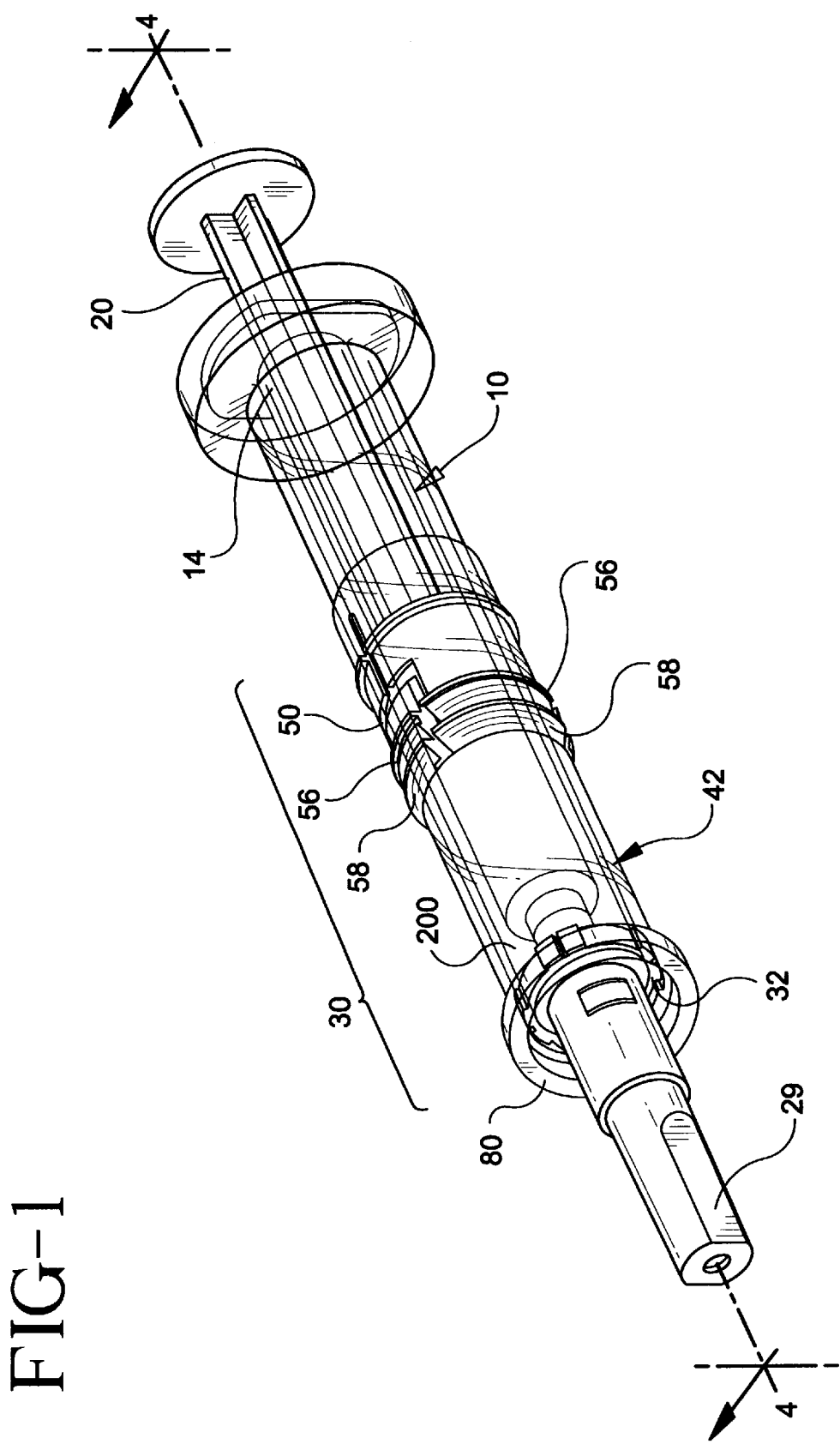
FIG. 1 depicts, in perspective view, a lockable safety shield assembly of the present invention mounted to a syringe.
Figure 2:
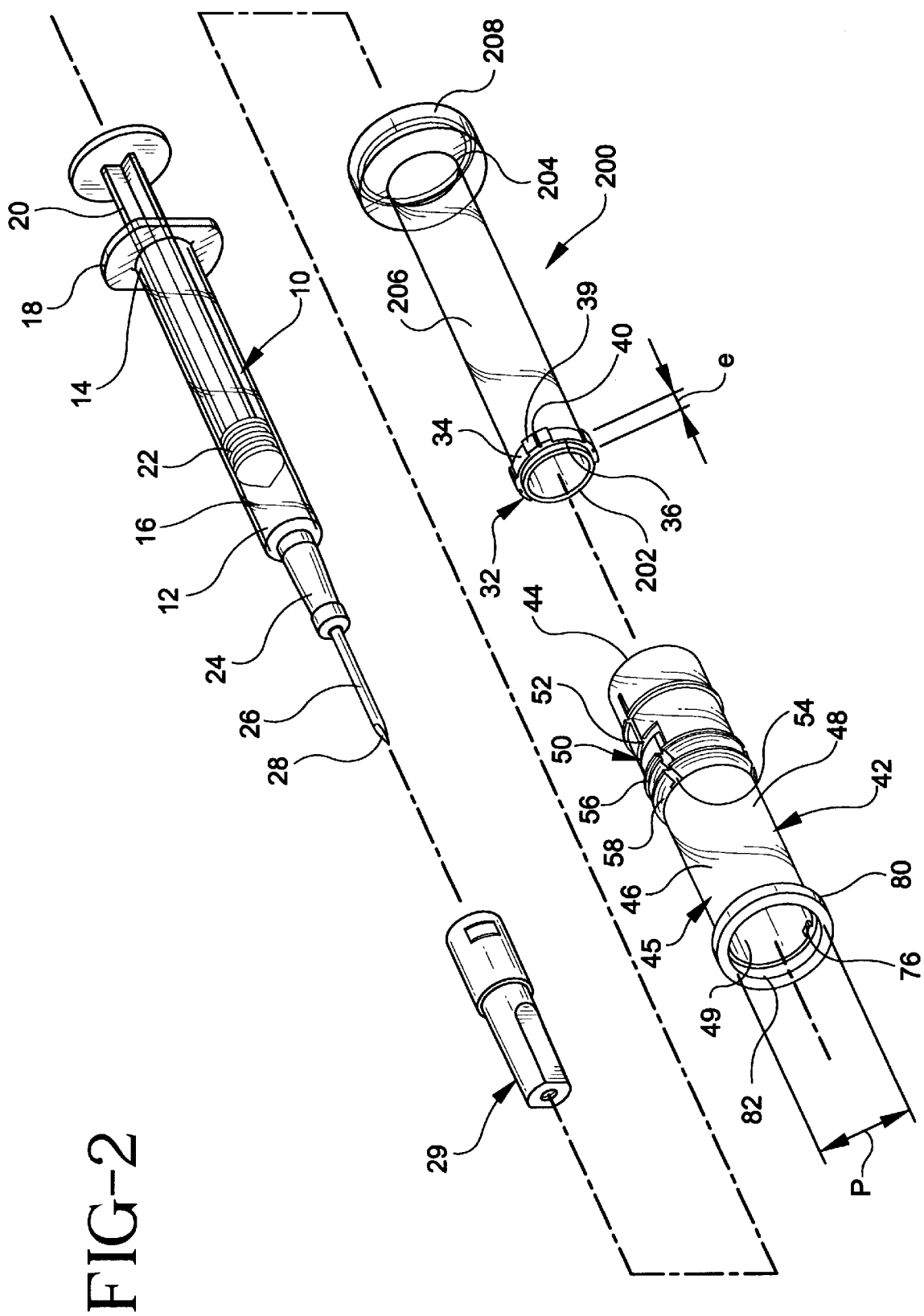
FIG. 2 is an exploded perspective view of the lockable safety shield assembly of FIG. 1.

Turning now to the drawings, wherein like numerals denote like components, FIGS. 1–4 depict one embodiment of a lockable safety shield assembly 30 in accordance with the present invention. The lockable safety shield assembly 30 in accordance with the present invention can be provided in conjunction with a prefillable syringe 10. As illustrated in FIGS. 1 and 2, prefillable syringe 10 includes a barrel 16 characterized by a proximal end 14, a distal end 12, and a hub 24 provided adjacent the distal end. A flange 18 may be provided about the proximal end, with a plunger rod 20 inserted through proximal end 14. Plunger rod 20 is attached to a stopper 22 used for urging fluid through barrel 16. Fluid is emitted or aspirated via a fluid path, structured at distal end 12 of the syringe, that communicates with interior portions of barrel 16. For instance, if the pre-fillable syringe is configured as a luer lock syringe, the fluid path is configured as a luer tip (not shown) provided at distal end 12. Here, pre-fillable syringe 10 is illustrated with a fluid path configured as a piercing element 26, such as a pointed needle cannula. Piercing element 26 is characterized by a distal end 28.

Figure 3:
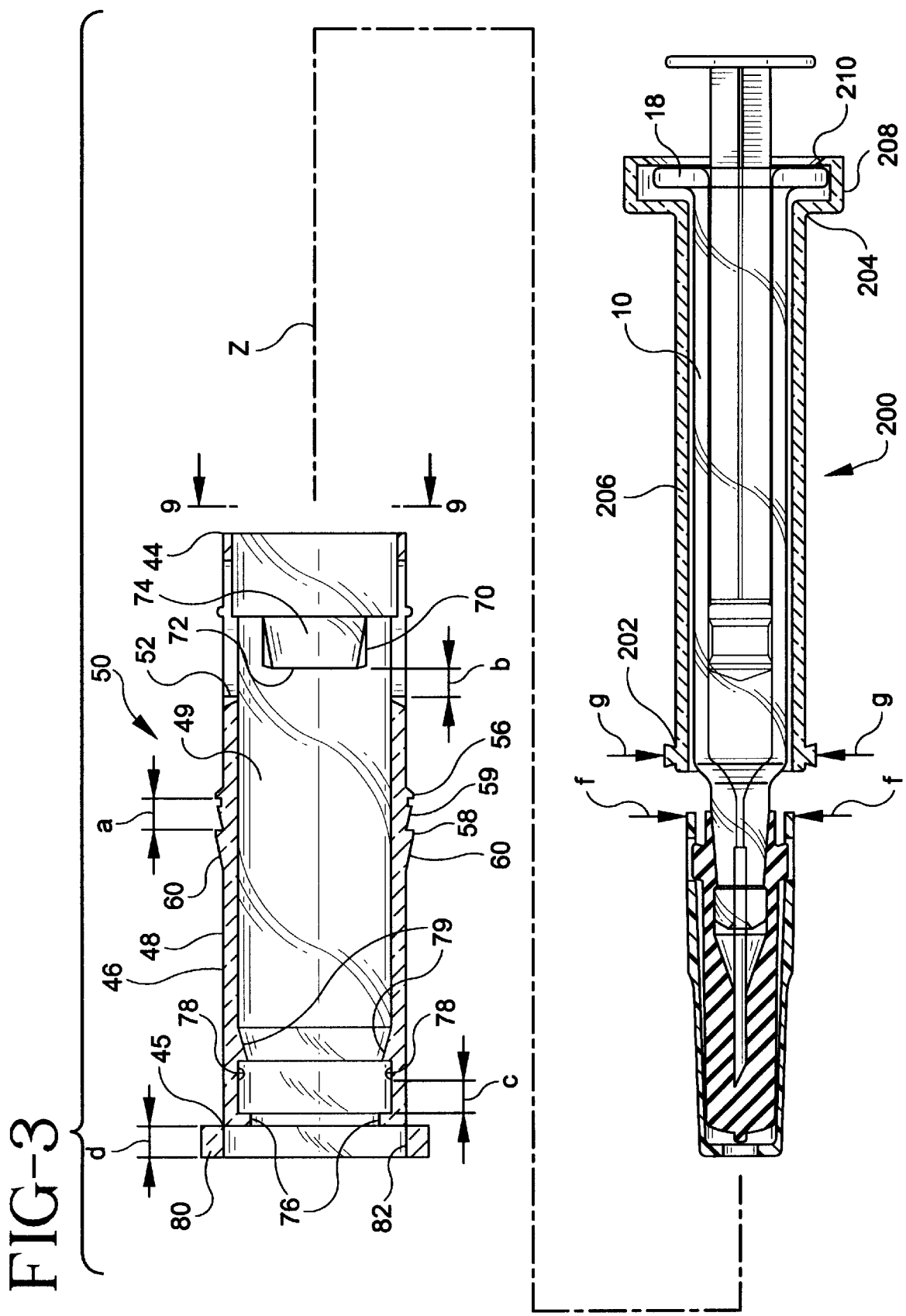
FIG. 3 is a cut-away view of the lockable safety shield of the present invention being mounted over the tube and the syringe barrel.

The lockable safety shield assembly 30 in accordance with the present invention includes a tube 200 which is mounted about barrel 16 of the syringe. The tube 200 features a proximal end 204, a distal end 202, and a circumferential sidewall 206 therebetween. A flange structure 208 is provided adjacent proximal end 204 of the tube. As best seen in FIG. 3, flange structure 208 includes a lip 210 sized to lockingly engage flange 18 of the syringe barrel when tube 200 is placed over barrel 16. Adjacent distal end 202 of the tube there is provided a collar 32. Collar 32 can be formed as a disk-like structure characterized by an edge 34 and a side portion 36. Collar 32 has a thickness "e" and is characterized by a maximum diameter "g". Collar 32 may be provided as part of the structure of tube 200. Alternately, as the skilled artisan will appreciate, collar 32 may be separately supplied and retained to the tube by friction fit, adhesives, mechanical means, or like structure. If desired, edge 34 can display one or more raised nubs 39 having grooves 40. Grooves 40 can be aligned with complementary rails (not shown) provided on an interior portion of safety shield 42 for aligning the safety shield during the assembly process.

For purposes of clarity, FIGS. 1–6 depict collar 32 as having a rectangular cross-section, with side portion 36 displaying relatively flat walls that are directly linked to edge 34. If so desired, collar 32 can be configured in this manner to construct a lockable safety shield assembly in accordance with the present invention. However, FIG. 10 depicts a preferred way for configuring the collar (here designated by the numeral 32a) so to provide better audible as well as tactile indication that shield 42 has been locked to the collar, as well as to enhance locking action between the shield and the collar, as will be further explained.

Figure 10:
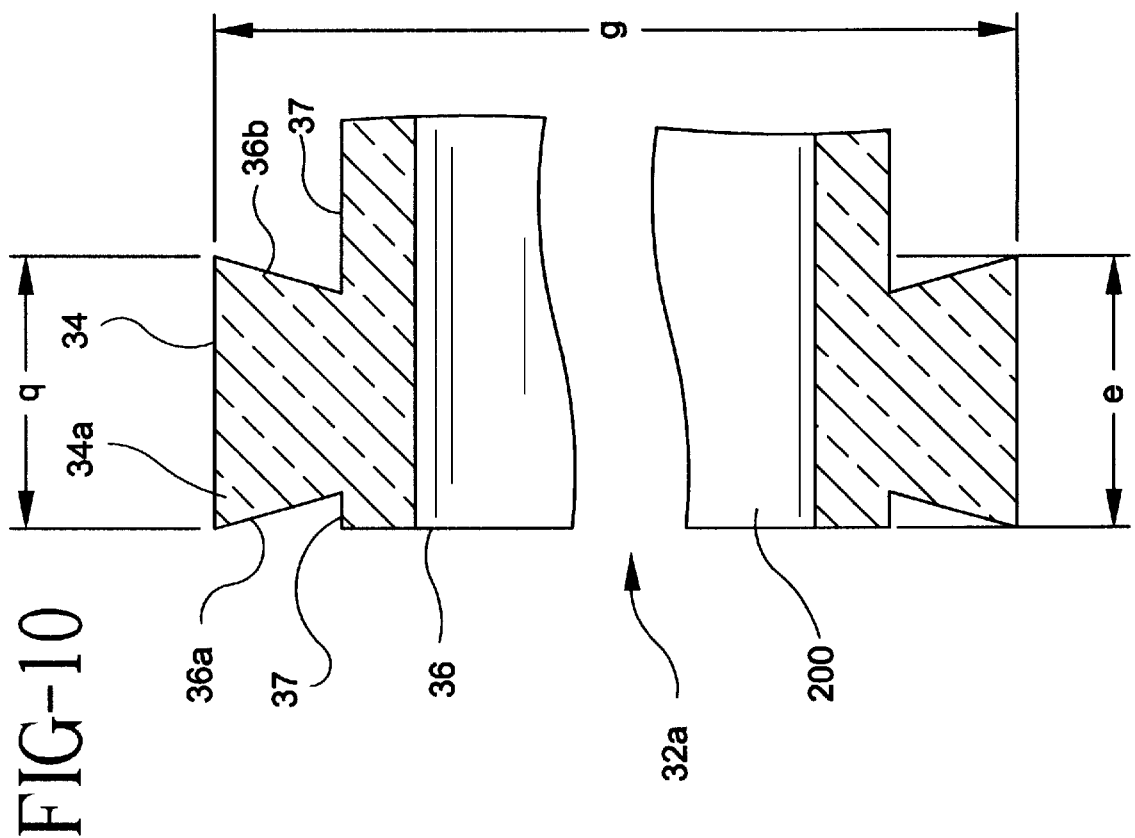
FIG. 10 is a partial cross-sectional view of a preferred manner of configuring the collar in accordance with the present invention.
Figure 9:
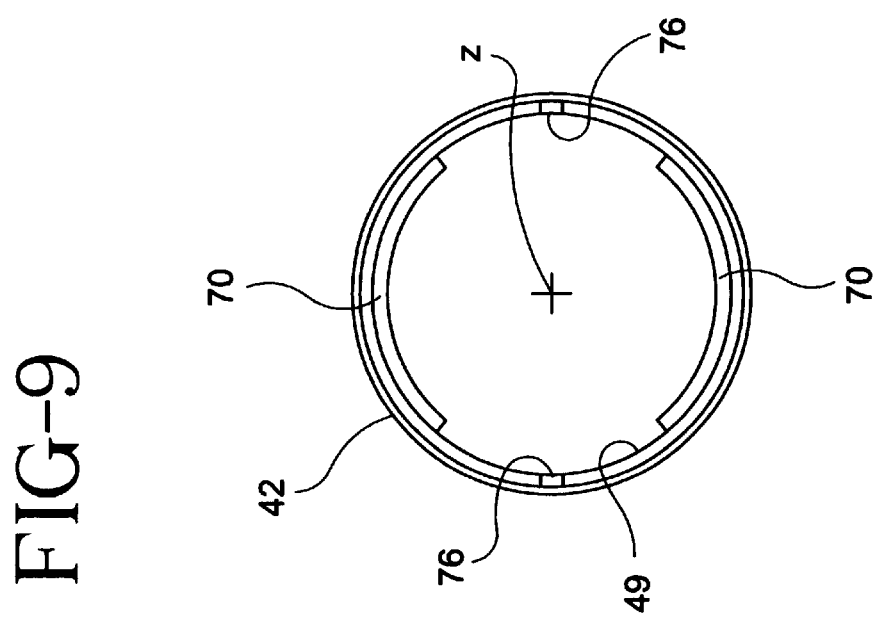
FIG. 9 is an end elevational view of the lockable safety shield assembly in accordance with the present invention.

Referring then to FIG. 10, as before, collar 32a includes an edge 34 and a side portion 36. However, here, side portion 36 is not completely flat. Rather, when viewed in cross-section, edge 34 and side portion 36 are linked by a locking tooth 34a. Locking tooth 34a features a distally-facing canted edge 36a and a proximally-facing canted edge 36b. Each of canted edges 36a, 36b of the locking tooth terminate at a shelf 37 that intersects with side portion 36. As before, if desired, grooves (not shown) can be provided on edge 34, for the purposes previously explained. As before, collar 32a includes a thickness "e" and a maximum diameter "g". Locking tooth 34a includes a maximum width "q" which need not be equal to thickness "e" displayed by collar 32a.

Safety shield 42 is characterized by a proximal end 44, a distal end 45, and a circumferential sidewall 46 therebetween. Circumferential sidewall 46 includes an outside surface 48 and an inside surface 49. Outside surface 48 is characterized by a diameter "N". Shield 42 is slidable both over tube 200 and collar 32, and thus over syringe barrel 16, between a retracted position (FIGS. 1,4 and 5), wherein distal tip 28 of piercing element 26 is exposed, and an extended position (FIG. 6), wherein the distal tip of the piercing element is protectively covered.

Lockable safety shield assembly 30 in accordance with the present invention includes user-activatable locking structure. A feature of the lockable safety shield assembly in accordance with the present invention is that the locking structure can be implemented such that it is not "activated" during assembly of the components, making it easier to assemble the components to syringe 10. Subsequent to assembly of the components, the locking structure can be "activated", putting the safety shield assembly in a ready-to-use state.

Making reference to FIGS. 1–3 and 7–9, shield 42 features at least one deflectable arm 50. Arm 50 is preferably provided as part of the structure of the shield. Arm 50, which may be molded as part of the shield or thereafter created from the shield via various cutting processes, includes a distal end 54 and a proximal end 52. Distal end 54 is resiliently affixed to sidewall 46 such as by a living hinge arrangement, while proximal end 52 is not attached to the sidewall and is configured for free movement towards an interior portion of shield 42. In a preferred embodiment, at least two deflectable arms 50 are provided on shield 42, with these two arms 50 located on diametrically-opposite sides of shield 42. Arms 50 are thus configured for a free position (FIGS. 1 and 4), wherein the surface of the arms are substantially co-planar with circumferential sidewall 46 of the shield, and a locking position (FIGS. 5, 7, and 8), wherein proximal ends 52 of arms 50 are urged towards the interior of the shield.

Figure 8:
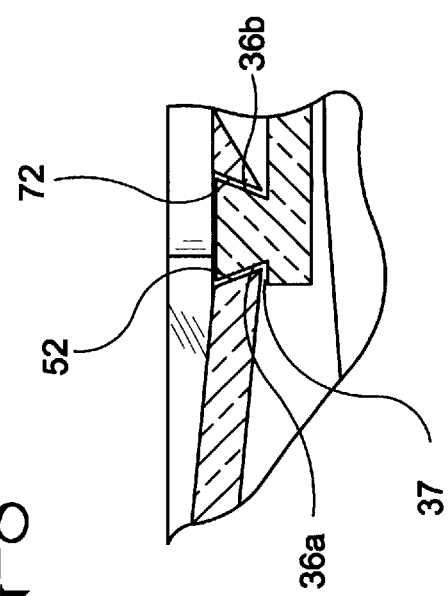
FIG. 8 is a partial cross-sectional view of the lockable safety shield assembly of the present invention interacting with the collar located on the tube.
Figure 7:
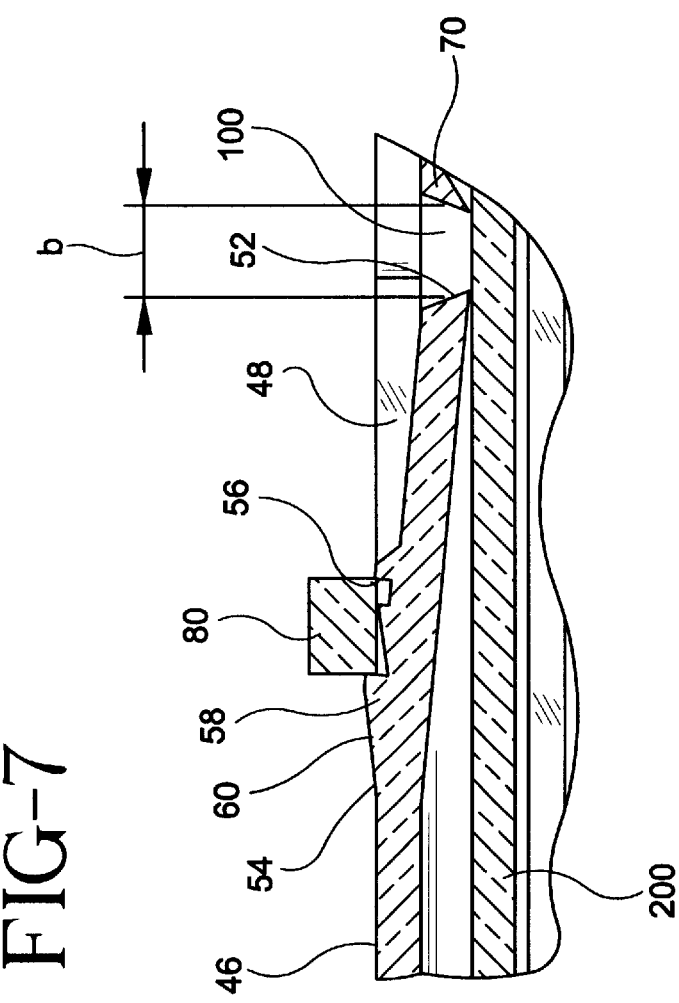
FIG. 7 is partial cross-sectional view of the lockable safety shield assembly of the present invention illustrating activation of the locking mechanism.

As best reflected by FIGS. 7 and 8, in a preferred configuration, proximal ends 52 of the deflectable arms are not straight. Rather, to best make use of the features of collar 32a (FIG. 10), proximal ends 52 are preferably canted in a manner such that when the deflectable arms are positioned towards the interior of the shield, the proximal ends will be oriented to lockingly cooperate with distally-facing canted edge 36a of collar 32a, as will be explained hereinbelow.

At least one stop member 70 is provided on inside surface 49 of the shield in an area adjacent proximal end 44. In a preferred embodiment, two stop members 70 are provided, each corresponding to a respective one of two deflectable arms 50 (see FIG. 9). Stop member 70 includes a distally-facing stop surface 72. Stop surface 72 is preferably spaced from proximal end 52 of the deflectable arm a distance "b" as measured along central axis "z" of the shield (see FIG. 3).

As best illustrated in FIGS. 7 and 8, in a preferred configuration, stop surface 72 is preferably not straight. Rather, to best make use of the features of collar 32a (FIG. 10), stop surface 72 is preferably canted in a manner such that it will lockingly cooperate with proximally-facing canted edge 36b of collar 32a, as will be explained hereinbelow.

Stop member 70 also includes a proximally-facing sloped surface 74. Proximally-facing sloped surface 74 facilitates sliding of shield 42 over collar 32 when the shield is assembled to tube 200. Stop member 70 can be located such that stop surfaces 72 are circumferentially aligned with respective proximal ends 52 of deflectable arms 50, when viewed along central axis "Z" of the shield. Alternately, if desired, stop members 70 can be placed on interior surface 49 of the shield such that they are circumferentially offset from respective proximal ends 52 of the deflectable arms, when viewed along central axis "Z" of the shield.

Figure 4:
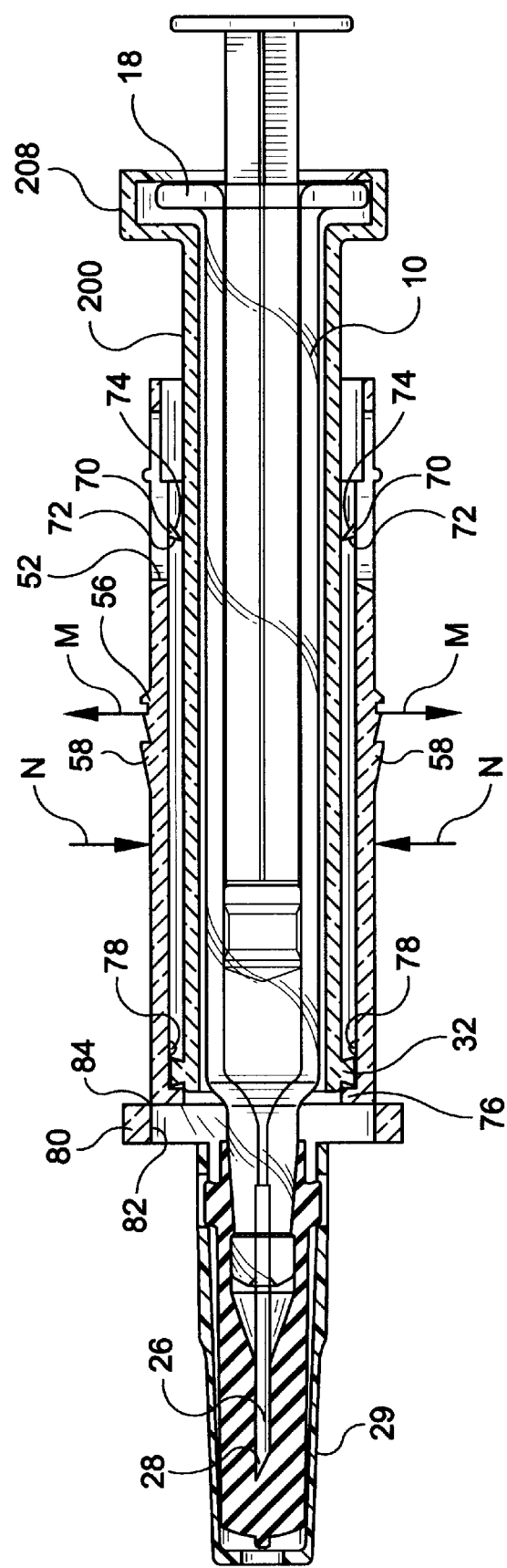
FIG. 4 is a cross-sectional view of the lockable safety shield assembly of the present invention subsequent to mounting to the syringe.

Shield 42 includes structure permitting activation of the deflectable arms 50 into their locked position (FIGS. 5,6,7, 8). A respective pair of distal and proximal abutments 58, 56 are provided on deflectable arms 50. Distal abutment 58, which includes a distally-facing sloped surface 60, is spaced from proximal abutment 56 by a distance "a" that defines a gap 59. As seen in FIGS. 3 and 4, in a preferred embodiment where two diametrically opposite deflectable arms are included, the diametrically opposite pair of gaps 59 define a diameter "M" slightly greater than diameter "N" defined by outside surface 48 of she shield when the arms 50 are in their free position. The effect is that gap 59 is configured so that it is elevated from the level of surrounding outside surface 48 of cylindrical sidewall 46 prior to activation of deflectable arm 50.

A circumferential ring 80 having an inside wall 82 is disposed for coaxial movement with circumferential sidewall 46 of the shield. Inside wall 82 has a diameter "P" at least equal to, if not greater than, diameter "N" defined by the outside surface of shield 42. Ring 80 has a width "d" at least equal to, if not slightly less than, the width of gap 59 as defined by distance "a". To simplify later assembly, shield 42 is typically configured with ring 80. Ring 80 can be retained to shield 42, for instance, by a user-severable connection. That is to say, shield 42 and ring 80 are preferably supplied to the pharmaceutical manufacturer as a single unit. For example, ring 80 can be supplied by the component manufacturer such that it is secured to the shield by a user-severable connection such as a threaded connection. Preferably, and as is disclosed herein, ring 82 is secured to distal end 45 of the shield by one or more user-severable connections 84 configured as thinned, frangible sections of material between ring 80 and proximal end 45 of the shield, thereby permitting easy removal of the ring from the shield for further assembly operations. This type of structure also permits the component manufacturer to easily form ring 80 and shield 42 as a single molding.

Shield 42 further includes structure for retaining shield 42 in the retracted position without being inadvertently "over-retracted" with respect to syringe 10 and, hence, inadvertently removed from syringe 10 in the proximal direction. As seen in FIG. 3, one or more distal stop members 76 can be provided on interior surface 49 of the shield adjacent distal end 45. Distal stop members 76 are configured to engage a distally-facing side portion 36 of the collar to prevent shield 42 from being over-retracted in a proximal direction. If desired, one or more tertiary stop members 78 can be provided on shield 42, each spaced from a respective distal stop member 76 by a distance "c" approximately equal to thickness "e" of collar 32. Hence, collar 32 can be releasably retained between distal stop members 76 and tertiary stop members 78 when the shield is in its retracted position. If desired, tertiary stop member 78 can be provided with a proximally-facing sloped surface 79 which, like proximally-facing sloped surface 74 associated with stop members 70, assists in the assembly of shield 42 about collar 32.

Operation of a device will now be explained.

As seen in FIG. 3, means can be fitted to the syringe adjacent the distal end to provide a barrier to the fluid path leading to the medicament which will be contained within barrel 16. The barrier is normally fitted by the syringe manufacturer and here, can be fitted to the syringe barrel in a process subsequent to placement of collar 32. If the fluid path is structured as a luer tip, for instance, a luer tip cap can be fitted. Here, where a piercing element 26 is configured on the syringe, a well-known needle shield 29 can be fitted about piercing element 26 so that a proximal-end of needle shield 29 rests against collar 32. Collar 32 should be configured such that maximum diameter "g" is at least slightly greater than a maximum diameter "f" displayed by needle shield 29, such that needle shield 29 will not interfere between operation of collar 32 and shield 42.

Preferably, safety shield assembly 30 is preassembled by the component manufacturer and presented to the pharmaceutical company in a sterile state, ready to be fit to the syringe once filled with the drug. Syringe 10 is supplied to the pharmaceutical manufacturer in a sterile state, ready to be filled with a desired drug and otherwise processed in a well-known manner. For instance, various filling operations, particulate inspection operations, labeling operations, plunger rod assembly operations may be conducted on the syringe.

As a first step in assembling the safety shield assembly, shield 42 is fitted to tube 200. Proximally-facing sloped surfaces 74 and, if provided, 79, assist shield 42 to smoothly surpass edge 34 of the collar. Shield 42 is slid over tube 200 in a proximal direction, such that collar 32 rests against distal stop members 76. If tertiary stop members 78 are provided, collar 32 will be releasably retained between distal stop members 76 and tertiary members 78. After the various filling and processing operations have been conducted on the syringe, tube 200 is slid over syringe barrel 16 such that flange 18 of the syringe is captured by lip structure 210 of the tube. As the shield is held to the tube in a retracted position, with needle shield 29 affixed to piercing element 26 will project beyond the distal end 202 of the tube. Syringe 10, together with lockable safety shield assembly 30, can be shipped by the pharmaceutical manufacturer to an end-user in a ready-to-use state.

Figure 5:
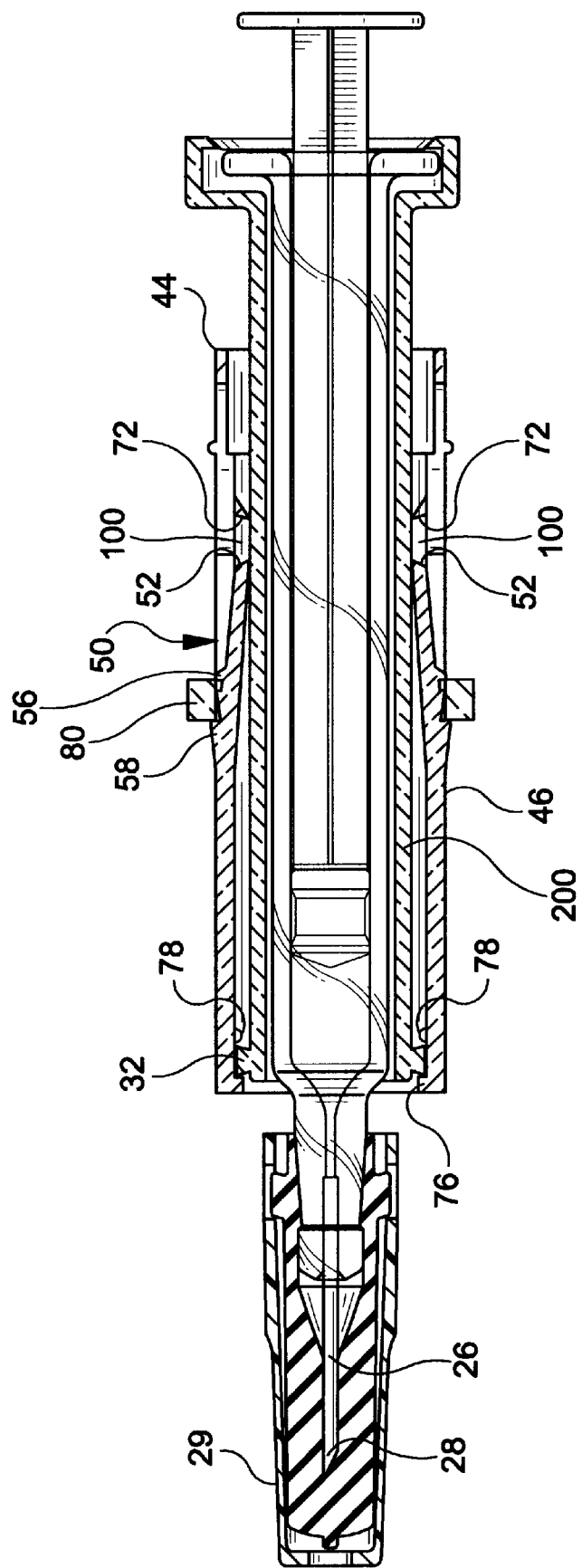
FIG. 5 is a cross-sectional view of the lockable safety shield assembly of the present invention after an end user has activated the locking mechanism.

FIG. 4 is representative of safety shield 42 of the present invention mounted about syringe 10 prior to activation of locking structure, while FIG. 5 is representative of the same construction after activation of the locking structure. Preferably, a pharmaceutical manufacturer will ship the prefillable syringe to the end-user in the state shown in FIG. 5, such that the locking structure is pre-activated. One way to do this is that the locking structure may be activated by the component manufacturer, as a final step in the preassembly of the safety shield assembly 30. For instance, the step of sliding ring 80 towards gap 59 can be effected as a final step in an assembly motion during which shield 42 is fitted to tube 200. In this vein, it will also be realized that because the component manufacturer preferably supplies the ring and shield to pharmaceutical manufacturer as a preassembled, single unit, the later assembly operations by the pharmaceutical manufacturer are simplified, in that the pharmaceutical manufacturer need only be concerned with sorting, orienting, distributing and then assembling a single unit about the syringe. Alternately, of course, it will be realized that the activation step can be done by the pharmaceutical manufacturer itself, as part of the operation in fitting the safety shield assembly to the syringe.

Nonetheless, FIG. 5 illustrates activation of the locking structure, whether by the component manufacturer, by the pharmaceutical manufacturer or by an end-user. The user-severable connections 84 connecting ring 80 to distal end 45 of the shield have been severed, and ring 80 has been slid proximally with respect to shield 42. Aided by distally-facing sloped surface 60 associated with distal abutment 58, inside surface 82 of the ring glides along outside surface 48 of the shield, over distally-facing sloped surface 60, and is secured in gap 59 defined between distal abutment 58 and proximal abutment 56. Because inside diameter "P" of ring 80 is smaller than diameter "M" between diametrically-opposed gaps 59, ring 80 exerts an inwardly-directed force upon deflectable arms 50. Deflectable arms 50 are thus deflected about their distal ends 54, such that proximal ends 52 are pushed towards the interior of shield 42. As a deflectable arm 50 is urged inwardly (see particularly FIGS. 7 and 8), proximal end 52 of a given deflectable arm and stop surface 72 of a respective stop element 70 define a gap 100 between them. Gap 100 is designed to "capture" collar 32 when the shield is slid distally to cover piercing element 26. Where the collar has a flat side portion 36, then gap 100 should have a width "b" at least equal, if not slightly greater than, thickness "e" of the collar to securely retain collar 32 in gap 100. If, as depicted in FIG. 10, the collar is configured with locking tooth 34a, then width "b" should be chosen so as to accommodate the maximum width "q" associated with locking tooth 34a, so that locking tooth 34a is securely retained in gap 100.

Figure 6:
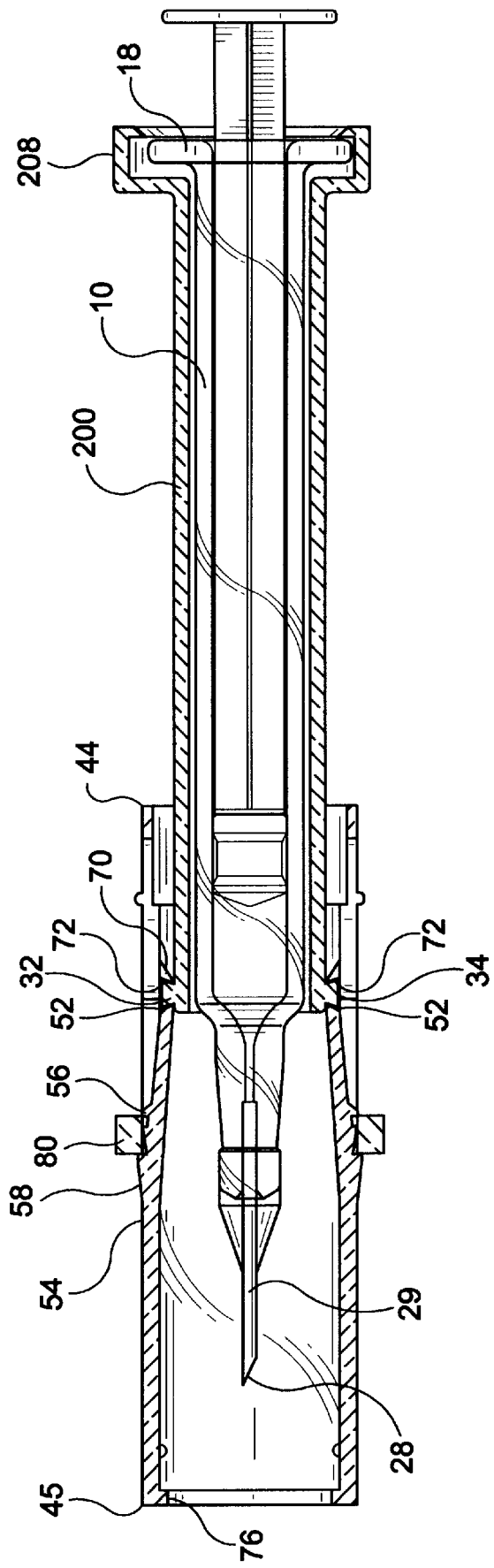
FIG. 6 is a cross-sectional view of the lockable safety shield assembly of the present invention after it has been urged in a distal direction by an end-user to protectively cover the needle cannula.

FIG. 6 is representative of shield 42 in its extended position to protectively cover distal tip 28 of the piercing element. After needle shield 29 has been removed and an injection administered in the usual manner, shield 42 is grasped by an end-user and slid distally with respect to syringe 10. Collar 32, which is fixed to tube 200, will thus be urged towards proximal end 44 of the shield. Owing to the resiliency of deflectable arms 50, edge 34 of the collar will push arms 50 in an outward direction from the interior of the shield and thus will pass along the length of arms 50. Edge 34 will eventually deflect past proximal end 52, causing the arm to re-deflect in an inward direction toward the interior of the shield. An audible indication, such as a clicking sound, will be heard to indicate activation of the safety mechanism. Thus, collar 32 will come to rest in gap 100, with the collar sandwiched between proximal end 52 and stop surface 72. Collar 32 is thus lockingly held between stop surface 72 and proximal end 52 of the arm, arresting further movement of the shield in either proximal or distal directions respective of syringe 10. Accordingly, shield 42 is retained in its extended position with respect to piercing element 26, protectively covering distal tip 28 against inadvertent touch contact.

As previously explained, in a preferred configuration (FIGS. 7, 8 and 10), deflectable arms 50, stop members 70 and collar 32a are configured to provide good audible as well as tactile indication that shield 42 has been locked to collar 32a. As edge 34 of collar 32a clears proximal end 52 of the deflectable arm, locking tooth 34a enters gap 100. As soon as the locking tooth enters gap 100, the resilient characteristics of the deflectable arm cause the arm to re-deflect in an inward direction toward the interior of the shield. At this moment, an interior portion 49a of deflectable arm 50 that is located adjacent proximal end 52 is thrust against shelf 37 of collar 32a. As soon as interior portion 49a is thrust against shelf 37, tactile as well as audible sensations are transmitted to the user, signaling that shield 42 has been locked to collar 32a. Owing to the canted orientations of both proximal end 52 of the deflectable arms and stop surface 72 of the stop members 70, each of the proximal ends 52 and stop surfaces 72 are lockingly retained against their respective distally facing canted edge 36a and proximally-facing canted edge 36b, such that tooth 34a is securely locked within gap 100. Thus, by a simple distal movement, shield 42 is self-locking with collar 34a.

Figure 11:
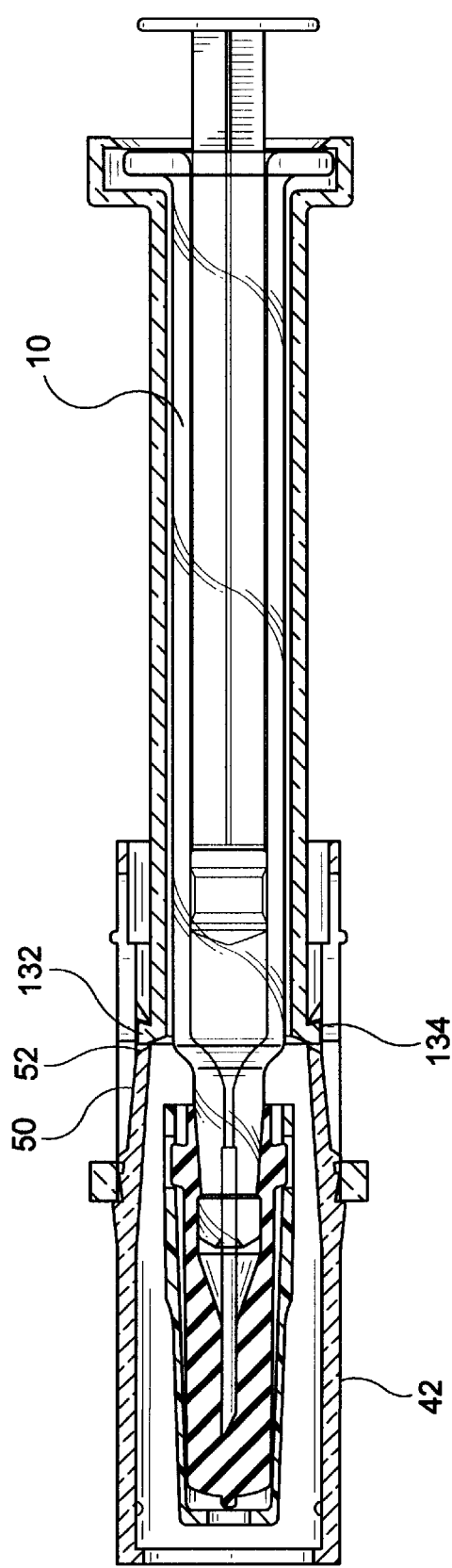
FIG. 11 is a cross-sectional view of an alternative embodiment of the lockable safety shield assembly of the present invention after it has been urged in a distal direction by an end-user to protectively cover the needle cannula.
Figure 12:
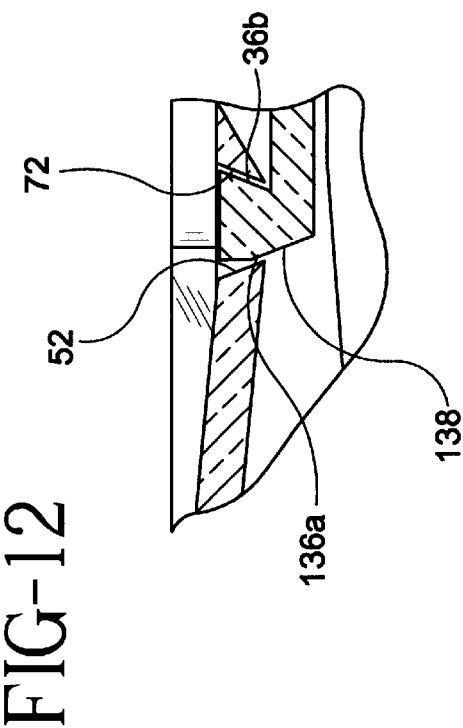
FIG. 12 is an enlarged, partial cross-sectional view of the alternative embodiment of the lockable safety shield assembly illustrated in FIG. 11 interacting with the collar located on the tube.
Figure 14:
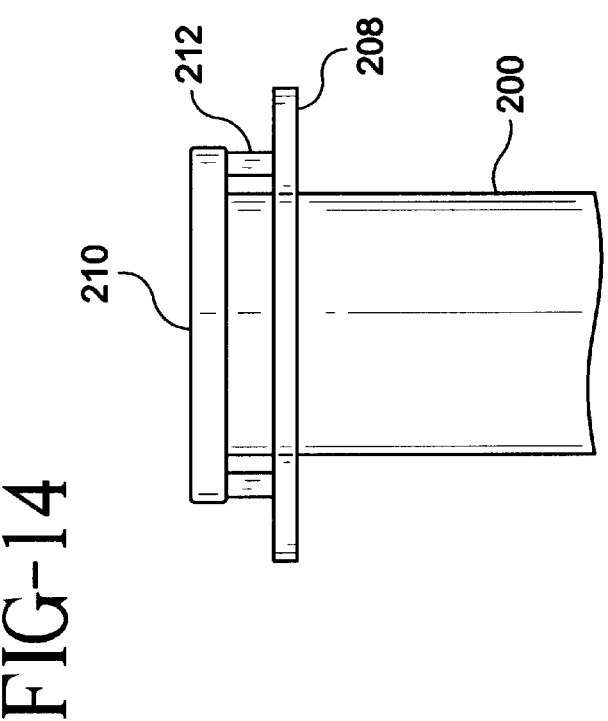
FIG. 14 is a fragmentary side view of the flange portion of the an alternative embodiment of the lockable safety shield assembly illustrated in FIG. 13.
Figure 13:
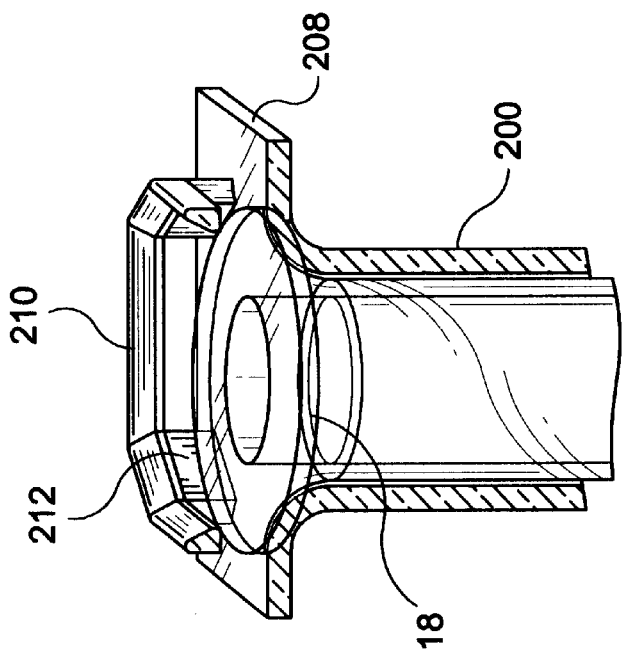
FIG. 13 depicts, in perspective, a partial cross-sectional view of an alternative embodiment of the lockable safety shield assembly of the present invention mounted to a syringe.
Figure 16:
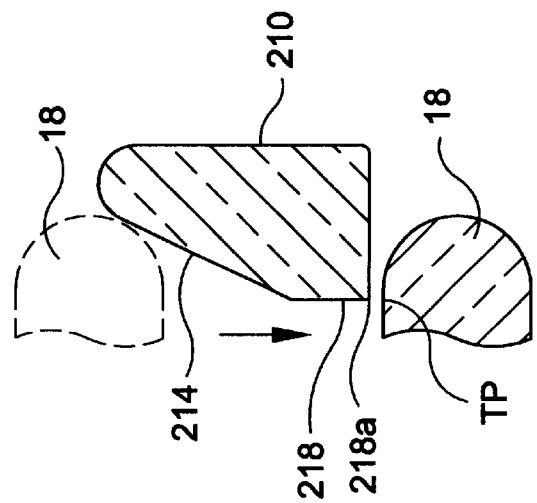
FIG. 16 depicts a fragmentary schematic representation of the insertion of the syringe into the flange portion of the lockable safety shield assembly illustrated in FIG. 13.
Figure 15:
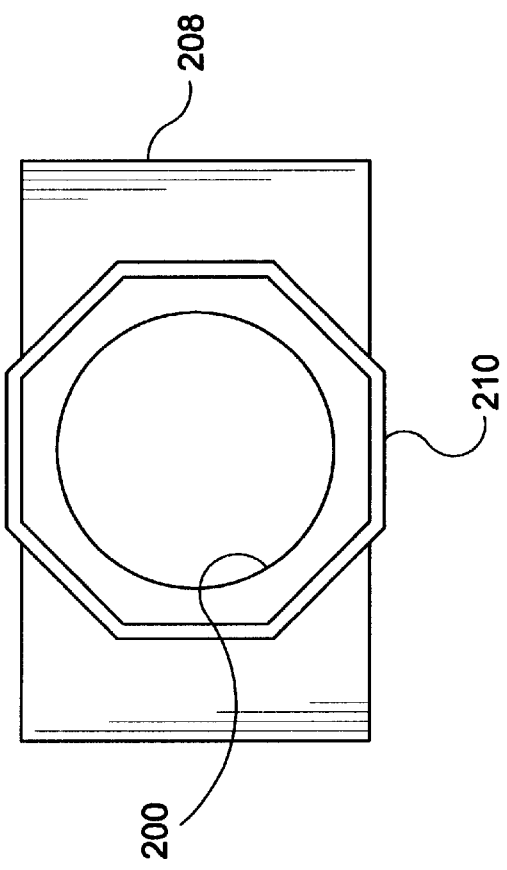
FIG. 15 is a fragmentary planar view of the flange portion of the an alternative embodiment of the lockable safety shield assembly illustrated in FIG. 13.

Referring then to FIG. 11, and FIG. 12 for greater detail, an alternative preferred embodiment of the collar 132 is illustrated, with the collar including an edge 134 and a side portion 136. However, here, side portion 136 is not completely flat. Rather, when viewed in cross-section, edge 134 and side portion 136 are not linked by a locking tooth. Instead, the side portion 136 includes a substantially flat abutting surface 136a and a distally-facing sloped surface 138. In this way, as proximal end 52 of the deflectable arm 50 is thrust towards the tube it abuts surface 136a of collar 132. Owing to the canted orientations of both proximal end 52 of the deflectable arms and sloped surface 138, if safety shield 42 is trust against the tube 200, the proximal end 52 each will travel along sloped surface 138 towards the syringe 10 thereby preventing exposure of the needle.

In another alternative preferred embodiment, as shown in FIGS. 13 through 16, the flange 208 of the tube 200, includes an upper proximal collar 210 spaced apart from said flange and supported on the flange by a plurality of posts 212. Preferably, the collar 210 has a polygonal shape, with an inwardly-sloping edge 214 along its inner surface and terminating a shoulder 218. In this way, as the syringe 10 is inserted into the tube 200, the flange 18 of the syringe comes in contact with the edge 214 causing the collar 210 to flex as the flange travels along the ridge. Once past the shoulder 218, the collar 210 is resilient enough to return to its resting position with the leading edge 218a of the shoulder extending beyond point at which the curved surface of the flange 18 transitions to the planar surface TP. In this way, the leading edge 218a will not readily come in contact with the curved portion of the flange so that the syringe cannot be easily removed from safety shield assembly 30.

The various components can be formed from suitable materials, such as medical-grade plastics or the like. They may be injection molded in manners well-known to the skilled artisan, resulting in reliable and cost-effective production of the locking shield assembly. The locking shield assembly of the present invention can be adapted with prefillable syringes of various dimensions and capacities. Various enhancements can be provided to permit easy assembly. For instance, sections of the sidewall adjacent the proximal end of the shield can be thinned, or slits can be incorporated in an area of the shield between the proximal end of the shield and the proximal edge of the deflectable arms, all to enhance the easier sliding of the shield proximally over the collar. Of course, the dimensions for the various components can be selected such that when the shield is in its retracted position, the distal tip of the piercing element is exposable for an injection, and when the shield in its extended position, the distal tip of the piercing element will be protectively covered to enable the end user to safely discard the syringe.

It will be appreciated and understood by those skilled in the art that further and additional revisions to the invention may be devised without departing from the spirit and scope of the appended claims, the invention not being limited to the specific embodiments shown.

What is claimed is:

1. A medical device, comprising:
   a barrel having proximal and distal ends;
   a tube secured about the barrel, the tube having a collar positioned adjacent the distal end of the barrel, the collar having an edge; and
   a shield mounted about said tube and axially movable between a retracted position, wherein the distal end of the barrel is exposed, and an extended position, wherein the distal end of the barrel is covered, the shield having a proximal end, a distal end, and a circumferential sidewall therebetween, the circumferential sidewall having an outside surface and an inside surface;
   user-activatable locking means to secure the shield in the extended position, the user activatable locking means comprising
      at least one deflectable arm having a distal end mounted with the circumferential sidewall and a proximal end deflectable towards the interior of the shield, said at least one arm having a free position wherein the arm is substantially coplanar with the circumferential sidewall of the shield, and a locking position, wherein the arm is deflected towards the interior of said shield so that the proximal end is positioned towards the interior of the shield,
      at least one stop member mounted to the interior surface of the shield adjacent the proximal end of the shield to define a gap between the stop member and the proximal end of the deflectable arm, and
      a ring axially slidable around the outside surface of the shield between a first position wherein the ring is spaced away from the at least one deflectable arm and a second position wherein the ring is positioned against said at least one deflectable arm to secure the arm in the locking position.

2. The medical device of claim 1, wherein the barrel includes a piercing element at its distal end, wherein the piercing element is exposed when the shield is in the retracted position, and wherein the piercing element is protectively covered when the shield is in the extended position.

3. The medical device of claim 1, wherein a flange is provided adjacent the proximal end of the barrel, the tube secured to the barrel at the flange of the barrel.

4. The medical device of claim 1, wherein said ring is secured to the distal end of the shield by a user-severable connection in the first position, wherein an end user may sever the user-severable connection to axially slide the ring to the second position.

5. The medical device of claim 1, wherein the stop member includes a proximally-facing sloped surface and a distally facing stop surface, the gap defined between said stop surface and the proximal end of said at least one deflectable arm.

6. The medical device of claim 1, wherein said deflectable arm comprises structure for retaining the ring in the second position.

7. The medical device of claim 6, wherein the structure for retaining comprises a distal abutment and a proximal abutment spaced from said distal abutment, wherein said ring is retained in the space between said proximal and distal abutments.

8. The medical device of claim 7, wherein the space between said proximal and distal abutments is raised from the surface of said at least one deflectable arm, wherein said space is substantially co-planar with the circumferential sidewall of the shield when said deflectable arm is in the locking position.

9. The medical device of claim 7, wherein said distal abutment includes a distally-facing sloped surface, wherein said ring is urged over the distally-facing sloped surface of the distal abutment into said second position.

10. The medical device of claim 1, wherein said shield further comprises a second stop located on the interior surface of the shield adjacent the distal end, said second stop engageable with the collar when said shield is in the retracted position.

11. The medical device of claim 10, further comprising a third stop located on the interior surface of the shield proximally of the second stop, wherein the edge of the collar is retained between the second and third stops when said shield is in the retracted position.

12. The medical device of claim 1, wherein a locking tooth is provided on the edge of the collar.

13. The medical device of claim 12, wherein the proximal end of the at least one deflectable arm is oriented for locking engagement with the locking tooth of the collar.

14. The medical device of claim 1, wherein a distally-facing inclined surface is provided on the edge of the collar facing at least one deflectable arm.

15. The medical device of claim 1, wherein said tube includes a flange and a collar spaced from said flange.

16. The medical device of claim 15, wherein said collar is supported on said flange by a plurality of posts.

17. The medical device of claim 15, wherein said collar has a generally polygonal shape with an inwardly-sloping edge along an inner surface.

18. A medical device, comprising:
a barrel having proximal and distal ends;
a piercing element extending from the distal end of the barrel and having a distal tip;
a flange provided adjacent the proximal end of the barrel;
a tube mounted about the barrel and secured to the flange, the tube having a collar positioned adjacent the distal end of the barrel, the collar having a side portion and a circumferential edge; and
a shield mounted about said tube and axially movable between a retracted position, wherein the distal tip of the piercing element is exposed, and an extended position, wherein the distal tip of the piercing element is covered, said shield having a proximal end, a distal end, and a circumferential sidewall therebetween, the circumferential sidewall having an outside surface and an inside surface, the shield including user activatable locking means to secure the shield in the extended position, the user activatable locking means comprising
at least one deflectable arm having a distal end mounted with the circumferential sidewall, a proximal end deflectable towards the interior of the shield, and an outside surface therebetween, the proximal end of the deflectable arm defining an edge for engaging said collar, said at least one arm having a free position wherein the outside surface of said arm is substantially coplanar with the circumferential wall of the shield, and a locking position, wherein said arm is deflected towards the interior of said shield so that said edge is positioned towards the interior of the shield, said deflectable arm including a pair of abutments on the outside surface spaced apart from one another,
at least one stop member mounted to the interior surface of the shield adjacent the proximal end of the shield to define a gap between the stop member and the proximal end of the deflectable arm, and
a ring retained to the shield by a user-severable connection, said ring axially slidable around the outside surface of the shield between a first position wherein the ring is spaced away from the at least one deflectable arm and a second position wherein the ring is positioned between the pair of abutments on said at least one deflectable arm to secure the arm in the locking position,
wherein the ring is slid proximally along the shield until the ring is positioned between the pair of abutments, and the shield thereafter urged distally so that the circumferential edge of the collar enters into the gap defined between the stop member and the proximal end of the arm so that the edge of the arm engages the collar.

19. The medical device of claim 18, wherein a locking tooth is provided on the circumferential edge of the collar.

20. The medical device of claim 19, wherein the edge of the arm is oriented for locking engagement with the locking tooth of the collar.

21. The medical device of claim 20, wherein the edge is canted.

22. The medical device of claim 18, wherein said stop member includes a proximally-facing sloped surface, wherein said shield is slidable proximally over said collar to place the shield in said retracted position.

23. The medical device of claim 18, further comprising at least one slit in said circumferential sidewall intermediate the proximal end of the shield the proximal edge of the deflectable arm.

24. The medical device of claim 18, wherein the circumferential sidewall defines a thickness between the inside surface and the outside surface, wherein the thickness of the sidewall adjacent the proximal end of the shield is less than the thickness of the sidewall intermediate the proximal and distal ends of the shield.

25. The medical device of claim 18, wherein the pair of abutments on the at least one deflectable arm includes a proximal abutment and a distal abutment, the distal abutment including a distally-facing sloped surface to facilitate passage of the ring over the distal abutment for placement between the pair of abutments.

26. The medical device of claim 18, wherein the edge of said at least one deflectable arm is shaped so that it is oriented parallel to the side portion of said collar when the deflectable arm is in said locked position.

27. The medical device of claim 18, wherein said shield further comprises a second stop located on the interior surface of the shield adjacent the distal end, said second stop engageable with the side portion of the collar when said shield is in the retracted position.

28. The medical device of claim 27, further comprising a third stop located on the interior surface of the shield proximally of the second stop, wherein the collar is retained between the second and third stops when said shield is in the retracted position.

29. The medical device of claim 18, wherein said third stop comprises a proximally-facing sloped surface to facilitate passage of ring over said third stop as the shield is positioned towards its retracted position.

30. The medical device of claim 25, wherein the space between said proximal and distal abutments is raised from the surface of said at least one deflectable arm, wherein said space is substantially co-planar with the circumferential sidewall of the shield when said deflectable arm is in the locking position.

31. The medical device of claim 30, wherein the space between said proximal and distal abutments is sloped, wherein the space is substantially co-planar with the circumferential sidewall of the shield when said deflectable arm is in the locking position.

32. The medical device of claim 18, wherein the user-severable connection comprises one or more thinned sections of material between said ring and the distal end of the shield.

33. The medical device of claim 18, wherein the user-severable connection comprises one or more thinned sections of material between said ring and the distal end of the shield.

34. A medical device, comprising:
   a barrel having proximal and distal ends;
   a piercing element extending from the distal end of the barrel and having a distal tip;
   a tube attached about the outside surface of the barrel, the tube having a collar positioned adjacent the distal end of the barrel, the collar having an edge and a locking tooth defined at the edge; and
   a shield mounted about said tube and axially movable between a retracted position, wherein the distal tip of the piercing element is exposed, and an extended position, wherein the distal tip of the piercing element is covered, the shield having a proximal end, a distal end, and a circumferential sidewall therebetween, the circumferential sidewall having an outside surface and an inside surface;
   user-activatable locking means to secure the shield in the extended position, the user activatable locking means comprising
      at least one deflectable arm having a distal end mounted with the circumferential sidewall and a canted proximal end deflectable towards the interior of the shield for locking engagement with the locking tooth of the collar, the at least one arm having a free position wherein the arm is substantially coplanar with the circumferential sidewall of the shield, and a locking position, wherein the arm is deflected towards the interior of said shield so that the proximal end is positioned towards the interior of the shield,
      at least one stop member mounted to the interior surface of the shield adjacent the proximal end of the shield and having a canted stop surface, the stop member placed on the shield to define a gap between the canted stop surface and the canted proximal end of the deflectable arm, and
      a ring axially slidable around the outside surface of the shield between a first position wherein the ring is spaced away from the at least one deflectable arm and a second position wherein the ring is positioned against said at least one deflectable arm to secure the arm in the locking position,
   wherein after the ring has been placed in the second position, the shield is urged distally so that the locking tooth enters into the gap between the canted stop surface and the canted proximal end of the arm to lock the tooth in the gap.

35. The medical device of claim 34, wherein an audible indication is produced as the locking tooth enters the gap.

36. The medical device of claim 34, wherein a tactile indication is produced as the locking tooth enters the gap.

* * * * *